United States Patent [19]
Brueckner et al.

[11] 4,072,289
[45] Feb. 7, 1978

[54] AXIAL TOMOGRAPHY

[75] Inventors: Keith A. Brueckner, La Jolla; John H. Lewis, Los Angeles, both of Calif.

[73] Assignee: Xonics, Inc., Van Nuys, Calif.

[21] Appl. No.: 722,202

[22] Filed: Sept. 10, 1976

[51] Int. Cl.² .............................................. G03B 41/16
[52] U.S. Cl. ................................ 250/445 T; 250/490; 128/2 V; 364/414
[58] Field of Search ............... 250/445 R, 445 T, 490; 235/151.3; 128/2 V

[56] References Cited
U.S. PATENT DOCUMENTS

| 4,002,913 | 1/1977 | Le May | 250/445 T |
| 4,021,673 | 5/1977 | Bossaert | 250/445 T |

*Primary Examiner*—Craig E. Church
*Attorney, Agent, or Firm*—Harris, Kern, Wallen & Tinsley

[57] ABSTRACT

Analog method and apparatus for producing an axial tomographic image of an object, typically the human body, using a detector for receiving radiation along a plurality of sets of paths, with the sets of paths overlapping each other, and providing a plurality of sets of detector output signals. Prior art devices exist for producing the detector output signals, which signals are then manipulated in a digital computer to produce the desired image. In one embodiment of the present invention, the detector output signals are summed in a storage tube and the stored signals are read in an inversely proportional relation, providing another signal for storage in another storage tube which is then read with a Laplacian relation to give a video signal for display and/or recording. Optical and electrostatic storage systems are also disclosed.

33 Claims, 8 Drawing Figures

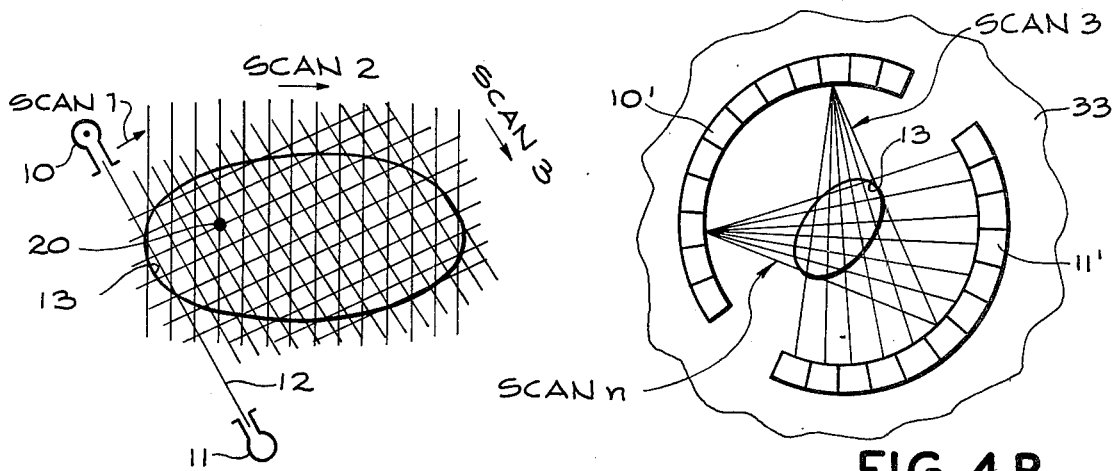
FIG. 1.
FIG. 4B.
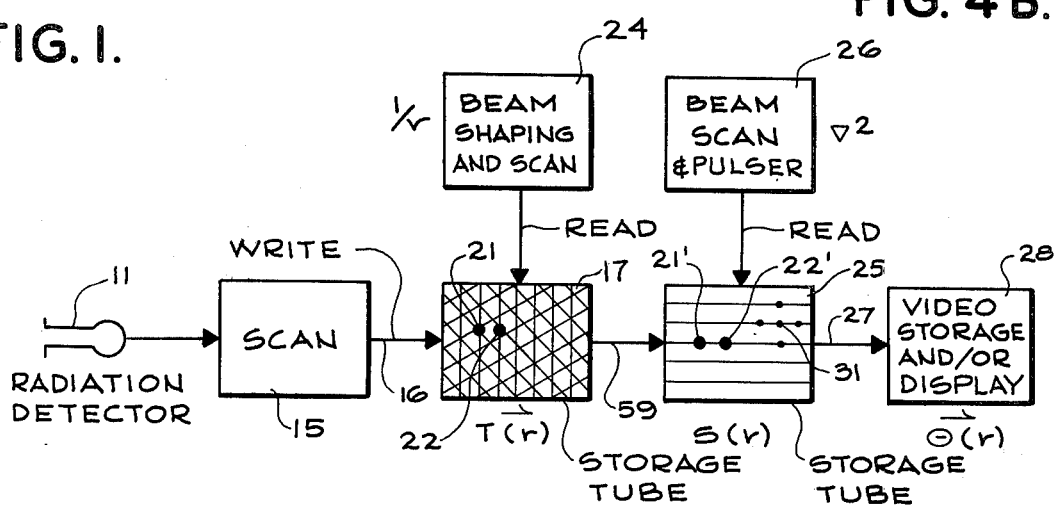
FIG. 2.
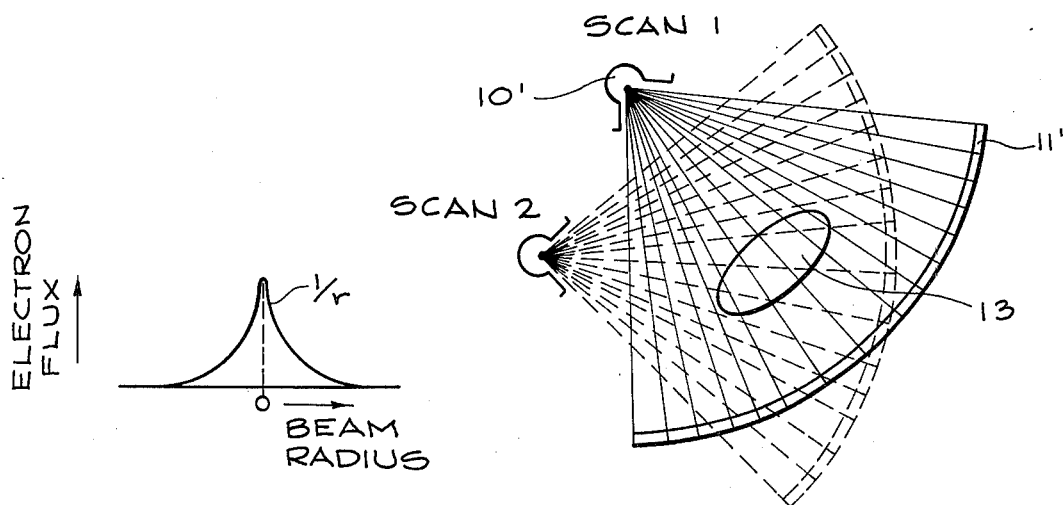
FIG. 3.
FIG. 4.

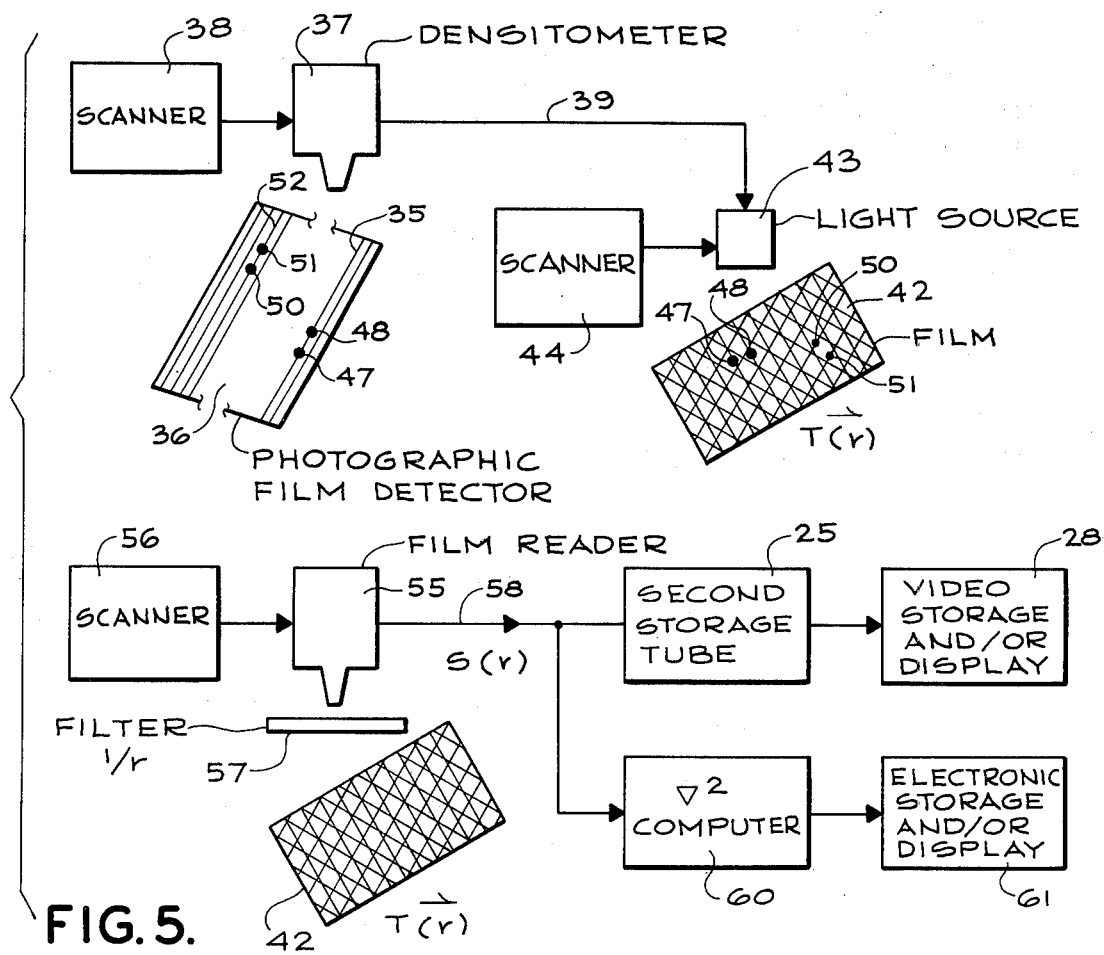
FIG. 5.
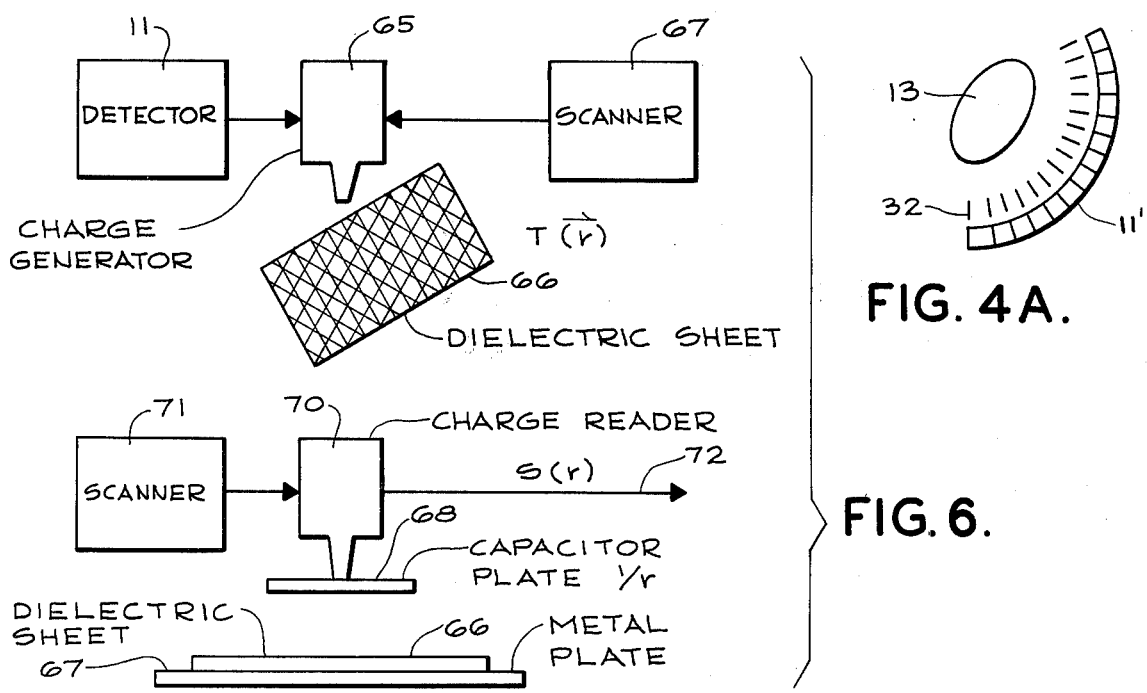
FIG. 4A.
FIG. 6.

AXIAL TOMOGRAPHY

BACKGROUND OF THE INVENTION

This invention relates to axial tomography, sometimes referred to as cross-sectional X-ray. A general discussion of the subject appears in the article "Image Reconstruction from Projections" by Richard Gordon, et al appearing in the October 1975 issue of Scientific American pages 56–68.

In a typical axial tomographic system, a detector receives radiation from an X-ray source along a plurality of sets of paths with at least some of the paths of a set traversing the object of interest, and with the sets of paths overlapping each other providing a plurality of sets of radiation detector output signals. These detector signals are then utilized in a complex computer operation to produce the desired image. This type of system is described in British Pat. No. 1,283,915, in the article "Theory of Image Reconstruction in Computed Tomography" by Rodney A. Brooks, et al appearing in Radiology 117: 561–572, December 1975, and in the article "Computerized Transaxial X-ray Tomography of the Human Body" by R. S. Ledley, et al appearing in Science, Oct. 18, 1974 Vol. 186 No. 4160.

These prior art systems utilizing a computer for data handling are relatively expensive because of the computer capacity required. Also, a significant amount of time is required in performing the computations for an image.

The prior art systems require digitizing of the detector output signals with a resultant loss in resolution. In order to improve resolution, one would have to increase the X-ray dosage which is undesirable in most instances. A typical prior art computerized axial tomography system will provide a display matrix of 180 bits by 180 bits for a brain section. In comparison, the analog system of the present invention utilizing a standard T-V monitor as the display can provide 1000 bits by 1000 bits for a brain section.

In addition, the prior art systems produce images which are degraded in quality if the object being radiographed is allowed to move, even in the slightest manner, during the sequential detection (scanning) process. Such motion causes the digital image reconstruction algorithms to produce artifacts which are difficult and time consuming to correct within the computer. In comparison, the analog system of the present invention does not suffer the same degree of difficulty, since such motion-induced artifacts are not generated during the analog image reconstruction process.

Accordingly it is an object of the present invention to provide a new and improved method and apparatus for axial tomography which may use the conventional radiation scanning configurations while improving resolution and image quality without requiring increases in X-ray dosage. A particular object is to provide such a method and apparatus which operates in an analog method rather than in a digital method, and an apparatus which is less expensive than the prior art systems.

An additional object of the present invention is to provide an analog method of image reconstruction which is applicable to tomographic images generally, whether produced by gamma ray, X-ray, or ultrasonic radiation. The detected quality of radiation can be either the transmitted X-ray beam which is a measurement of attenuation along a ray, as is the case of the prior art systems, or an emitted beam which is a measurement of source strength along a collimated ray, as is the case in nuclear medicine procedures. Ultrasonic radiation can be measured either as an intensity transmitted signal or as a temporal (time of flight) signal. The integrated velocity of the ultrasonic beam through the imaged object is a measure of the material dispersion as opposed to attenuation and constitutes additional information which can be imaged.

SUMMARY OF THE INVENTION

The apparatus of the present invention may utilize the conventional X-ray or ultrasonic source and detector and scanning mechanism for producing the plurality of sets of radiation detector output signals. The apparatus further includes means for storing the detector output signals in analog form with the signals of one set overlying the signals of another set so that signals resulting from radiation through a zone of the object being examined are summed at a corresponding zone in the storage device, which typically is an electronic storage tube. These summed signals are read from the storage device with a radially inversely proportional reader producing a second signal for storage, again typically in an electronic storage tube. These signals stored in the second storage device are read with a Laplacian relation, with the resultant signal being a video signal suitable for connection to a TV monitor for display of the sectional image. This display may be photographed for a permanent record and alternatively, the video signal may be recorded for a permanent record. In alternative embodiments, optical film systems and electrostatic systems are utilized.

The method of the present invention includes storing the detector output signals in analog form with signals of one set overlying signals of another set summing the signals resulting from radiation through a zone of the object being examined at a corresponding storage zone, as by writing the signals in an electronic storage tube or exposing a photographic film or generating charges on a dielectric. The summed signals are read in a radially inversely proportional relationship to provide a second signal which in turn is stored. The stored second signal is read with a Laplacian relation to provide an output which is a video signal corresponding to the desired sectional image.

BRIEF DESCRIPTION OF THE DRAWINGS

FIG. 1 diagrammatically illustrates one known form of axial tomography scanning utilizing a pencil beam;

FIG. 2 is a block diagram of an apparatus for using the detector output and incorporating the presently preferred embodiment of the invention;

FIG. 3 is a graph illustrating a preferred reading beam electron flux density for the first storage tube of the apparatus of FIG. 2;

FIG. 4 is a diagram similar to that of FIG. 1 illustrating a fan beam configuration;

FIG. 4A is a diagram illustrating a detector array with collimation;

FIG. 4B is a diagram illustrating operation with an ultrasonic source and detector;

FIG. 5 is a block diagram of an optical apparatus incorporating an alternative embodiment of the invention; and FIG. 6 is a block diagram of an electrostatic apparatus incorporating an alternative embodiment of the invention.

DESCRIPTION OF THE PREFERRED EMBODIMENTS

FIG. 1 illustrates a conventional scan configuration used in axial tomography. An X-ray source 10 produces a pencil beam directed to a radiation detector 11 along a path through the object (object path) 12. The X-ray source and detector are scanned across the object 13 providing radiation intensity measurements along a set of parallel paths, typically 100 paths. The scan mechanism is then rotated relative to the object, typically 1°, and a second scan is performed providing a second set of parallel paths. Three sets of such paths, scan 1, scan 2 and scan 3, are shown in FIG. 1. In the conventional axial tomography system, the detector output signals are digitized for use in computing the cross sectional image of the object 13.

In the presently preferred embodiment of the invention illustrated in FIG. 2, the detector 11 is scanned across the object by a scanner 15, with the detector output on signal line 16 being written into an electronic storage tube 17. The detector output signal for object path 12 is stored as a line in the storage tube, with the set of paths of a scan providing a set of lines at the storage tube. The detector output signal for the set of paths for the next scan are written as lines at the storage tube over the lines of the previous scan. Thus the detector output signals for any point in the object 13 are summed at a corresponding point at the storage tube 17. For example, the detector output signals for radiation passing through the point 20 of the object 13 are summed at the point 21 of the storage tube 17.

The signals now stored in the storage tube 17 are read by a scanner 24, typically using a conventional raster scan, with the output being stored in a second storage tube 25, with the signal at point 21' in the tube 25 corresponding to the signal at point 21 in the tube 17. Similarly, the signal at point 22' in the tube 25 corresponds to the signal at point 22 in the tube 17.

The signals at the storage tube 25 are read by another scanner 26 providing an output on signal line 27 in the form of a video signal suitable for display at a cathode ray tube 28 providing the desired reconstructed tomographic image of the object 13.

The directions of the image scans correspond to the geometry of the radiation source and detector, usually on an altered scale. The complete tomographic image is formed by the accumulation of the images for the complete rotation of the detector system. To avoid edge effects in the final processed image, the recorded tomographic image desirably should be approximately 50 to 100% larger in linear dimension than the expected size of the imaged object.

The tomographic image T at point $\vec{r}$ is closely equal to $$T(\vec{r}) = \int \frac{\theta(\vec{r}')}{|\vec{r} - \vec{r}'|} d\vec{r}' \tag{1}$$

with the integral carried over the two-dimensional object plane. The visual object $\theta(\vec{r})$ can be recovered from the tomographic image by the geometric process $$\theta(\vec{r}) = \Delta^2 S(r) \tag{2}$$

$$S(\vec{r}) = \int \frac{d\vec{r}' \, T(\vec{r}')}{|\vec{r} - \vec{r}'|} \tag{3}$$

The integral over $T(\vec{r}')$ giving $S(r)$ can be performed by a detector with response inversely proportional to distance from the scan point, which integrates the image intensity. The derivative of $S(r)$ required to form the image is determined by signal subtraction.

$$\Delta^2 S(r) = \text{constant} \times [S(x + \Delta, y) + S(x - \Delta, y) + S(x, y + \Delta) + S(x, y - \Delta) - 4 S(x, y)] \tag{4}$$

Thus the reconstructed object signal at $x$, $y$ is formed from the 5 measurements at the points $x \pm \Delta$, $y$; $x$, $y \pm \Delta$; $x$, $y$. This can be done by sequential shift of the integrator or by digital recording of the output for subsequent subtraction or by pulsed or focus modulated e-beam non-destructive reading of $S(r)$ reconstruction.

The electron beam of the scanner 24 is tailored to provide the desired inversely proportional relationship $1/r$. The desired electron flux density in the beam is illustrated in FIG. 3, with the electron flux density decreasing as the inverse of the distance from the center of the beam. This may be achieved using conventional techniques, such as fixed focus control shaped electron beam, or scanning between a focussed and a defocussed condition, or by means of a spiral pencil beam.

In the preferred embodiment illustrated, the Laplacian $\Delta^2$ may be obtained by utilizing a pulsed pencil beam. By way of example, for reading at the point 31, the beam may be pulsed 4 times at point 31 and 1 time at each of four surrounding points, with the readings for the signals at point 31 subtracted from the readings for the four surrounding points. Additionally there exists standard techniques for obtaining "Laplacian Enhancement" by modulating the focus of the scanning electron beam about the point of interest. The spiral pencil beam may be a pencil electron beam which is projected in a spiral of uniform angular velocity about the scan point providing the desired integrated reading which is inversely proportional to the radial distance of the beam from the scan point.

The present invention is not limited to the specific embodiment shown in FIGS. 1 and 2 and a variety of components may be utilized. By way of example, an X-ray source providing a fan beam may be utilized in place of the pencil beam. Also, an external X-ray source is not required and the system may be utilized with an object having one or more radiation sources within the object, such as is used in nuclear medicine techniques.

For nuclear medicine imaging, the detector should incorporate a collimating grid which limits the aperture and the emitted radiation beam. The detector may take various forms including scintillators, a strip of film, a continuous scintillator backed by a photocell array, a photo conductor/photo emitter sandwich such as CsI/SbCs, and an electron radiographic real time recorder. The radiation source and detector may be scanned in synchronism or one may be scanned with the other stationary. One alternative configuration is illustrated in FIG. 4, with radiation source 10' providing a fan beam of radiation to a detector 11'. This arrangement provides a set of converging radiation paths rather than the set of parallel paths of the configuration of FIG. 1. After exposure and recording of detector output signals along each path of the set, the source and detector are rotated relative to the object 13 to provide another scan, illustrated as scan 2 in FIG. 4. Typically, scans will be made at 1° intervals through 180° of rotation. When utilizing radioactive sources within the body under examination, collimation should be provided for the detector array, such as shown in FIG. 4A, where metal sheets 32 are positioned in front of the detectors of the array 11' to define a path to each detector element. An arcuate detector array as shown in FIG. 4 can be used to provide converging paths. Alternatively a linear array can be used to provide parallel paths. In another alternative, a collimated single detector may be scanned across the body either along a straight path or an arcuate path as desired.

While the preceeding discussion has referred to X-ray and gamma ray sources and detectors, the present invention is equally applicable to systems using ultrasonic sources and detectors. The attenuation of the ultrasonic beam or the reduction in velocity of the ultrasonic beam can be measured to provide the detector output signals. Both techniques are conventional.

Ultrasonic generators are considerably less expensive than X-ray sources, and an array 10' of ultrasonic signal generators may be used as shown in FIG. 4B, with the generators driven in sequence to provide the sets of paths through the body 13 to the detector array 11'. With this configuration there is no requirement for motion of the source or detectors. In ultrasonic systems, the source, detector and object may be immersed in a liquid medium 33 for improved energy coupling.

Several of these alternatives are illustrated in the embodiment of FIG. 5. A photographic film detector is utilized, with each scan of the object being recorded as a line 35 on the film 36. After development, the film is read by a densitometer 37 driven by a scanner 38 to provide the detector output signals on signal line 39. Each line 35 corresponds to a set of paths, with each point read along the line providing the output signal for a single path. The detector output signals at signal line 39 may be stored in a storage tube, such as the tube 17 of FIG. 2. However in the embodiment illustrated, the output signals are stored on another photographic film 42, with a line on the film 42 for each point on the film 36, producing the overlying set of lines. The film 42 may be exposed by a light spot source 43 which us scanned across the film by a scanner 44, with the light intensity varying as a function of the detector output signals on the signal line 39.

By way of example, points 47 and 48 of line 35 on film 36 will be used to produce lines 47 and 48 on the film 42. Similarly, points 50 and 51 of line 52 of film 36 will be used to produce lines 50 and 51 on the film 42. The signals stored on the film 42 correspond to the signals stored on the storage tube 17, with the summing being produced by the overlapping of the exposures.

The film 42 is developed and then may be read by another densitometer 55 driven by a scanner 56 which reads the summed signals along a set of paths, typically a conventional raster scan. The desired inversely proportional relationship may be obtained by using a filter 57 in the reader, with the filter having a transmission characteristic of $1/r$, where $r$ is zero at the optical axis of the reader 55.

The output of the reader 55 on signal line 58 is $S(r)$, corresponding to the output on signal line 59 of the embodiment of FIG. 2.

The signals on line 58 may be stored in the second storage tube 25 and then handled in the same manner as described in conjunction with the embodiment of FIG. 2. Alternatively, the signals may be connected to a mini-computer 60 where they are digitized, stored in a memory, and used in computing the Laplacian as shown in equation (4). The computed Laplacian is the desired image ready for storage and/or display at 61. Typical storage devices include video tapes and video discs. Typical display devices include cathode ray tubes, photographic film, and electrostatic printers.

An electrostatic system is utilized in the embodiment illustrated in FIG. 6, with the output signals from the detector 11 being used to drive an electrostatic charge generator 65 such as an electron beam which is scanned over a dielectric sheet 66 by a scanner 67 producing the overlying sets of paths corresponding to the pattern in the storage tube 17 of FIG. 2 and the film 42 of FIG. 5, producing the desired summed signals.

The charge pattern on the dielectric sheet 66 may be read by a capacitor type charge reader 70 which is driven by a scanner 71, typically in a raster scan. The dielectric sheet 66 may be placed on a metal plate 67 which serves as one plate of a capacitor, with the other plate 68 carried by the reader and having the plate 68 physically shaped to provide the inversely proportional relationship. The charge reader output on signal line 72 may be handled in the same manner as the reader output on the signal line 58 shown in FIG. 5.

Although exemplary embodiments of the invention have been disclosed and discussed, it will be understood that the embodiments disclosed may be subjected to various changes, modifications and substitutions without necessarily departing from the spirit of the invention.

The present invention provides high resolution and improved image quality with relatively low radiation dosage while eliminating the requirement for digital storage of the detector output signals and the expensive data processing both in terms of time and equipment required in the prior art systems for handling the digitized detector output signals.

We claim:

1. In an apparatus for producing an axial tomographic image of an object, with a detector for receiving radiation along a plurality of sets of paths, with said sets of paths overlapping each other, providing a plurality of sets of radiation detector output signals, the improvement including in combination:

first means for storing said detector output signals in analog form at a surface with signals of one set overlying signals of another set whereby the signals resulting from radiation through a zone of the object are summed at a corresponding zone at said surface producing a first stored signal;

first means for reading said first stored signal, including means for scanning across said surface and means for producing second signals, with a second signal for a scan point being a function of the magnitude of the first stored signal at the scan point and varying substantially inversely proportional to distance from the scan point;

second means for storing said second signals producing second stored signals; and second means for reading said second stored signals at each of a plurality of points of said second storage means and including means for producing a video signal for each point, with a video signal being substantially the Laplacian of the second stored signal for the point, and with the video signal corresponding to the desired image.

2. An apparatus as defined in claim 1 wherein said first means for storing includes an electronic storage tube.

3. An apparatus as defined in claim 2 wherein said first means for reading includes an electron beam of circular cross-section with the intensity of electron flux varying substantially inversely proportional to the distance from the center of the beam, with said beam being scanned across said surface reading said first stored signal.

4. An apparatus as defined in claim 2 wherein said second means for storing includes an electronic storage tube.

5. An apparatus as defined in claim 4 wherein said second means for reading includes a pulsed electron beam of substantially uniform electron flux density.

6. An apparatus as defined in claim 5 wherein said Laplacian is produced by summing the second stored signals for four points about the point of interest and four times the negative of the second stored signal at the point of interest.

7. An apparatus as defined in claim 4 wherein said second means for reading includes an electron beam and means for modulating the focus of said beam to vary the electron flux density and produce said Laplacian of said second stored signal.

8. An apparatus as defined in claim 2 wherein said first means for reading includes a pencil electron beam which is projected in a spiral of uniform angular velocity about the scan point to provide an integrated reading substantially inversely proportional to the radial distance from the scan point.

9. An apparatus as defined in claim 2 wherein said first means for reading includes an electron beam and means for modulating the focus of said beam to vary the intensity of electron flux substantially inversely proportional to the distance from the center of the beam, with said beam being scanned across said surface reading said first stored signal.

10. An apparatus as defined in claim 1 wherein said first means for storing includes a photographic film and a radiation source for exposing said film as a function of said detector output signals.

11. An apparatus as defined in claim 10 wherein said first means for reading includes a film density reader.

12. An apparatus as defined in claim 11 wherein said film density reader includes a filter with a center and a transmission characteristic varying substantially inversely proportional to distance from said center.

13. An apparatus as defined in claim 11 wherein said second means for storing includes an electronic storage tube.

14. An apparatus as defined in claim 11 wherein said second means for storing includes a computer memory.

15. An apparatus as defined in claim 14 wherein said second means for reading includes a computer which calculates said Laplacian using the second stored signals from said memory.

16. An apparatus as defined in claim 1 wherein said second means for storing includes a computer memory.

17. An apparatus as defined in claim 16 wherein said second means for reading includes a computer which calculates said Laplacian using the second stored signals from said memory.

18. An apparatus as defined in claim 1 wherein said first means for storing includes a dielectric sheet and an electrostatic charge source for charging said sheet as a function of said detector output signals.

19. An apparatus as defined in claim 18 wherein said first means for reading includes an electrostatic charge reader.

20. An apparatus as defined in claim 19 wherein said electrostatic charge reader is a capacitive type reader with a capacitor plate having a center and shaped to provide an output varying substantially inversely proportional to distance from said center.

21. An apparatus as defined in claim 1 wherein said second means for storing includes an electronic storage tube.

22. An apparatus as defined in claim 21 wherein said second means for reading includes a pulsed electron beam of substantially uniform electron flux density.

23. An apparatus as defined in claim 22 wherein said Laplacian is produced by summing the second stored signals for four points about the point of interest and 4 times the negative of the second stored signal at the point of interest.

24. A process for producing an axial tomographic image of an object utilizing the output of a detector which receives radiation along a plurality of sets of paths, with the sets of paths overlapping each other, producing a plurality of sets of radiation detector output signals, including the steps of:

storing the detector output signals in analog form with signals of one set overlying signals of another set summing the signals resulting from radiation through a zone of the object at a corresponding storage zone producing a first stored signal;

reading the first stored signal by scanning across the storage zones and producing second signals, with a second signal for a scan point being a function of the magnitude of the first stored signal at the scan point and varying substantially inversely proportional to distance from the scan point;

storing the second signal; and producing a electronic signal for each of a plurality of the second signals, with a electronic signal being substantially the Laplacian of the second signal and with the electronic signal corresponding to the desired image.

25. The process as defined in claim 24 in which the detector output signals are stored electronically in a storage tube.

26. The process as defined in claim 25 which the inversely proportional relation is obtained by controlling a scanning electron beam.

27. The process as defined in claim 24 in which the detector output signals are stored optically on a film.

28. The process as defined in claim 27 in which the inversely proportional relation is obtained by varying the intensity of a scanning illumination beam.

29. The process as defined in claim 24 in which the detector output signals are stored electrostaticly on a dielectric.

30. The process as defined in claim 29 in which the inversely proportional relation is obtained by varying the shape of a scanning capacitor plate.

31. The process as defined in claim 24 in which the Laplacian relation is obtained by computation of digitally stored second signals.

32. The process as defined in claim 24 in which the second signals are stored electronically in a storage tube.

33. The process as defined in claim 32 in which the Laplacian relation is obtained by controlling a pulsed uniform density scanning electron beam.

* * * * *

UNITED STATES PATENT AND TRADEMARK OFFICE
CERTIFICATE OF CORRECTION

PATENT NO. : 4,072,289
DATED : February 7, 1978
INVENTOR(S) : Brueckner, Keith A., Lewis, John H.

It is certified that error appears in the above-identified patent and that said Letters Patent are hereby corrected as shown below:

Column 3, Line 67, correct Eq. (2) as follows:

$$\theta(\vec{r}) = \nabla^2 S(r) \qquad (2)$$

Column 4, Line 12, correct Eq. (4) as follows:

$$\nabla^2 S(r) = [\text{constant}] [S(x + \Delta, y) + S(x - \Delta, y) + S(x, y + \Delta) + S(x, y - \Delta) - 4 S(x, y)] \qquad (4)$$

Column 4, Line 31, correct "$\Delta^2$" to -- $\nabla^2$ --

Signed and Sealed this

Eleventh Day of July 1978

[SEAL]

*Attest:*

RUTH C. MASON
*Attesting Officer*

DONALD W. BANNER
*Commissioner of Patents and Trademarks*